United States Patent [19]

Tagaya

[11] Patent Number: 4,924,530
[45] Date of Patent: May 15, 1990

[54] MEDICAL GLOVE

[76] Inventor: Mamoru Tagaya, 14-4-510 Gakuen-Nishimachi 2-chome, Kodaira-shi, Tokyo, Japan

[21] Appl. No.: 229,994

[22] Filed: Aug. 9, 1988

[30] Foreign Application Priority Data

Nov. 5, 1987 [JP] Japan .................. 62-168443[U]

[51] Int. Cl.⁵ .......................................... A41D 19/00
[52] U.S. Cl. ........................................ 2/163; 2/168
[58] Field of Search ............... 2/159, 161 R, 163, 167, 2/168, 169; D2/616, 617

[56] References Cited

U.S. PATENT DOCUMENTS

| | | | |
|---|---|---|---|
| 612,741 | 10/1898 | Longden | 2/168 |
| 919,406 | 4/1909 | Warren | 2/168 |
| 1,554,291 | 9/1925 | Peck | 2/168 |
| 2,266,716 | 12/1941 | Robertson | 2/168 |
| 2,335,871 | 12/1943 | Milligan | 2/167 |
| 2,670,473 | 3/1954 | Stebic | 2/159 |
| 3,197,786 | 8/1965 | Velonis | D2/617 |
| 4,064,564 | 12/1977 | Casey | 2/168 |
| 4,507,807 | 4/1985 | Karkanen | 2/163 |

FOREIGN PATENT DOCUMENTS

| | | | |
|---|---|---|---|
| 0664015 | 8/1938 | Fed. Rep. of Germany | 2/168 |
| 2089197 | 6/1982 | United Kingdom | 2/159 |

*Primary Examiner*—Werner H. Schroeder
*Assistant Examiner*—Diana L. Biefeld
*Attorney, Agent, or Firm*—Oblon, Spivak, McClelland, Maier & Neustadt

[57] ABSTRACT

A medical glove highly suitable for use for carrying out accurate medical treatment and capable of facilitating operation of the hand. The medical glove includes a tight-fitting section and a loose-fitting section. The tight-fitting section constitutes a least a thumb and a forefinger of a finger section of the glove and is adapted to tightly fit the thumb and forefinger of the hand. The tight-fitting section is formed of an elastomeric film material closely contacting with the fingers of the hand. The loose-fitting section constitutes the remaining part of the glove and loosely fits the remaining part of the hand.

10 Claims, 1 Drawing Sheet

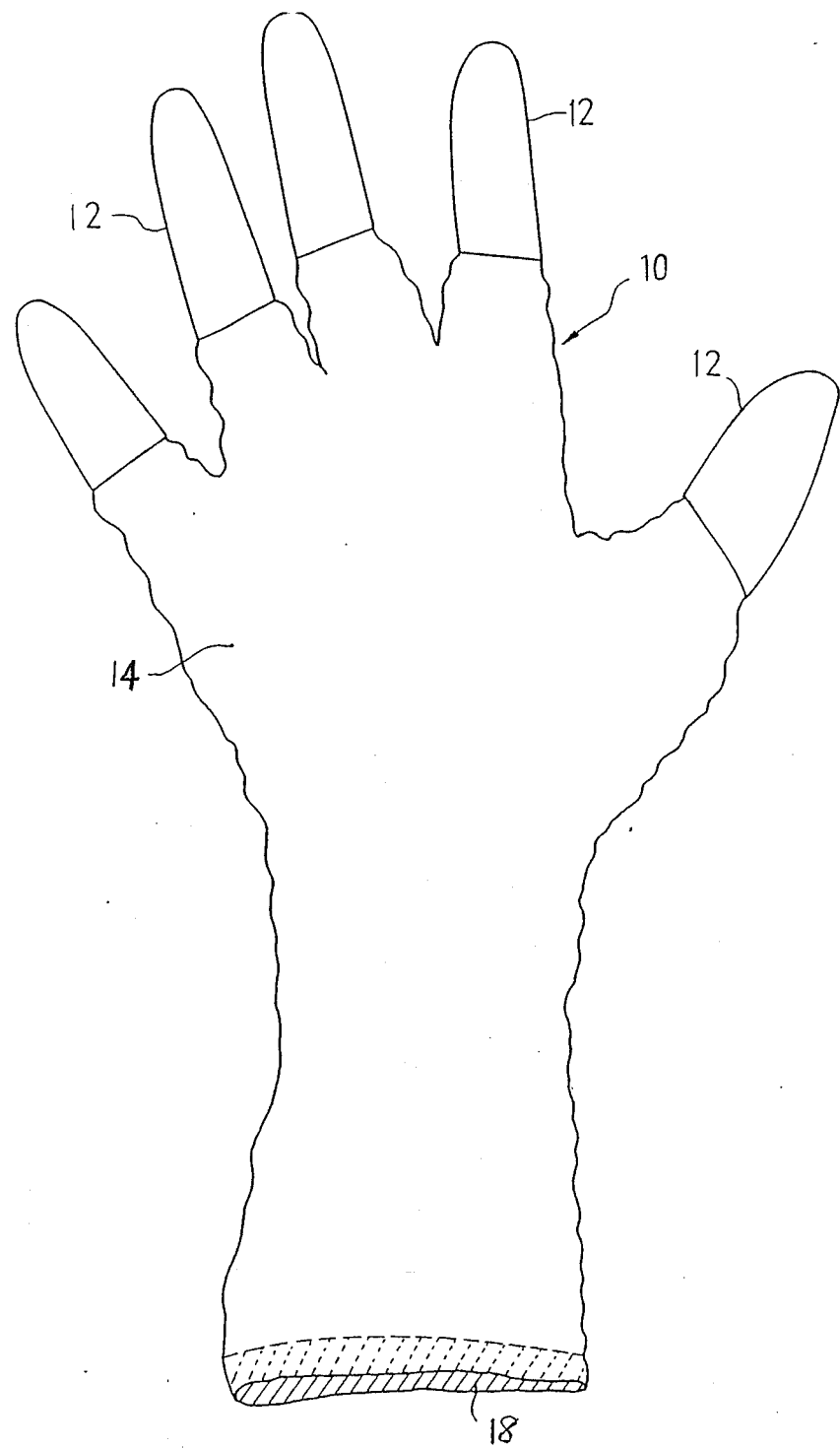

MEDICAL GLOVE

BACKGROUND OF THE INVENTION

1. Field of the Invention

This invention relates to a medical glove, and more particularly to a medical glove which medical personnel, such as doctors or the like, use during medical treatment, such as diagnoses, operations, or the like.

2. Description of the Prior Art

Hands are widely different in sizes and shapes depending on the individual. Unfortunately, a conventional medical glove which is standardized fails to satisfactorily fit the hand, and accordingly, medical people are apt to hesitate before using this glove because it may cause medical treatment, which must be carried out accurately, to fail.

Recently, a great interest has been taken in hepatitis B, AIDS (acquired immune deficiency syndrome) and the like. Medical people are obliged to carry out medical treatment, such as surgical operations or the like, while being exposed to such dangerous diseases. Accordingly, a medical glove is essential to medical people. Unfortunately, the conventional medical glove fails to fit the hand, particularly the fingers. Thus medical people cannot carry out medical treatment without anxiety.

Accordingly, it would be highly desirable to develop a medical glove which is capable of tightly fitting fingers, to a degree sufficient to allow medical people to carry out medical treatment free from anxiety and facilitating operation of the hand.

SUMMARY OF THE INVENTION

Generally speaking, in accordance with the present invention, a medical glove is provided. The medical glove includes a tight-fitting section which constitutes at least a thumb and a forefinger of a finger section of the glove and is adapted to tightly fit at least the thumb and forefinger of the hand. The tight-fitting section is formed of an elastomeric film material closely contacting with the fingers of the hand. The glove also includes a loose-fitting section constituting the remaining part of the hand. The tight-fitting section may be constructed to constitute a portion of each finger of the glove between its tip end and its second joint.

Accordingly, it is an object of the present invention to provide a medical glove which is capable of satisfactorily fitting and which has satisfactory tactual sense.

It is another object of the present invention to provide a medical glove which is highly suitable for use for accurate medical treatment.

It is a further object of the present invention to provide a medical glove which is capable of facilitating operation of the hand.

It is still another object of the present invention to provide a medical glove which is capable of minimizing hand fatigue.

It is yet another object of the present invention to provide a medical glove which is capable of exhibiting good air-permeability.

It is still a further object of the present invention to provide a medical glove which is capable of being applied to a wide variety of individual hand sizes and shapes.

Still other objects and advantages of the invention will in part be obvious and will in part be apparent from the specification.

The invention accordingly comprises the features of construction, combination of elements, and arrangement of parts which will be exemplified in the construction hereinafter set forth, and the scope of the invention will be indicated in the claims.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein:

the single FIGURE is a plan view showing an embodiment of a medical glove according to the present invention.

DESCRIPTION OF THE PREFERRED EMBODIMENT

A medical glove according to the present invention will be described hereinafter with reference to the single FIGURE.

A medical glove of an embodiment generally indicated at reference numeral 10 in the FIGURE generally includes a tight-fitting section 12 and a loose-fitting section 14. The tight-fitting section 12 constitutes at least a thumb and a forefinger of a finger section of the glove 10 and is adapted to tightly fit at least the thumb and forefinger of the hand. The tight-fitting section 12 may be formed of an elastomeric film material such as natural rubber, synthetic rubber, special rubber, polyethylene or the like which closely contacts with the fingers of the hand so that it may tightly fit the fingers of the hand. The loose-fitting section 14 constitutes the remaining part of the glove other than at least the thumb and forefinger of the glove and is adapted to loosely fit the remaining part of the hand.

As described above, in the present invention, the tight-fitting section 12 constitutes at least the thumb and forefinger of the glove. These are the fingers most frequently used in medical treatment, such as surgical operations or the like. However, the illustrated embodiment, as shown in the FIGURE, may be so constructed that the tight-fitting section 12 constitutes all fingers of the glove including the thumb and forefinger and the loose-fitting section 14 constitutes the base of each of the fingers and the remaining part of the glove, such as the palm.

The loose-fitting section 14 may be made of the same material as the tight-fitting section 12 or a suitable material different therefrom and conventionally used. Also, both sections may be formed together or separate from each other.

The tight-fitting section 12 made of an elastomeric film material is formed so as to fit the tip of each of the fingers. however, it is preferably formed so as to fit a portion of each finger between its tip and its second joint. Also, use of a transparent elastomeric film material for the tight-fitting section 12 helps provide satisfactory tactual sense, thus facilitating the discrimination of an implement held by the hand. However, the elastomeric film material used is not limited to that having transparency. It may be colored so long as it facilitates discrimination of the implement.

Also, in the illustrated embodiment, the medical glove may be provided on an inner surface of an open end thereof with an annular member 18 formed of a thin spongy material. Such construction effectively prevents sticky contact between the open end of the glove 10 and a wrist due to sweating and allows the glove to have good air-permeability.

The medical glove 10 of the illustrated embodiment constructed as described above may be formed into a shape in conformity with each hand. Alternatively, it may be formed into a shape common to both hands. Also, the medical glove 10 may be previously sterilized. Further, a lubricous powder material may be applied to the inside of the glove 10, particularly the inside of the tight-fitting section 12 to facilitate wearing of the glove.

The medical glove of the illustrated embodiment may be formed into a size corresponding to each of the existing standard rings, so that selection of a medical glove of a desired size may be carried out depending on the rings.

As can be seen from the foregoing, the medical glove of the present invention is so constructed that at least the thumb and forefinger of the glove are made of an elastomeric film material which tightly fits at least said thumb and forefinger of the hand and the remaining part of the glove is made into the loose-fitting section. The so-formed tight-fitting section causes the glove to exhibit a satisfactory fit with the hand and a satisfactory tactual sense. This results in the medical glove of the present invention exhibiting the advantage of being suitable for use for accurate medical treatment. Also, the medical glove of the present invention facilitates various operations carried out by the hand, such as picking-up thin needles, fine implements or the like, thus preventing damage of the glove by a needle or the like, and satisfactorily maintains the tactual sense of the fingers and prevents slippage of the glove. Also, the loose-fitting section of the glove allows hand fatigue to be minimized and the glove to exhibit both good air-permeability and an applicability to a wide variety of individual hand sizes and shapes.

It will thus be seen that the objects set forth above, among those made apparent from the preceding description, are efficiently attained and, since certain changes may be made in the above construction without departing from the spirit and scope of the invention, it is intended that all matter contained in the above description or shown in the accompanying drawings shall be interpreted as illustrative and not in a limiting sense.

It is also to be understood that the following claims are intended to cover all the generic and specific features of the invention herein described and all statements of the scope of the invention which, as a matter of language, might be said to fall therebetween.

What is claimed is:

1. A medical glove comprising:
   a tight-fitting section which comprises at least a thumb and a forefinger of finger sections of said glove and tightly fitting at least the thumb and forefinger of a hand, said tight-fitting section being formed of an elastomeric film material closely contacting with the thumb and forefinger of the hand and extending between their tips and at least a second joint thereof; and
   a loose-fitting section which comprises a remaining part of said glove and loosely fitting a remaining part of said thumb and said finger sections.

2. A medical glove as defined in claim 1, wherein said tight-fitting section comprises five fingers of said finger section of said glove.

3. A medical glove as defined in claim 1, wherein said elastomeric film material comprises a transparent material.

4. A medical glove as defined in claim 1, wherein a thin spongy material is disposed on an inner surface of said glove.

5. A medical glove as defined in claim 1, wherein said glove is of a shape common to both hands.

6. A medical glove as defined in claim 1, wherein said glove comprises a sterilized glove.

7. A medical glove as defined in claim 1, wherein said tight-fitting section and loose-fitting section are formed so as to be integral with each other.

8. A medical glove as defined in claim 1, wherein said tight-fitting section and loose-fitting section comprise the same material.

9. A medical glove as defined in claim 1, wherein said tight-fitting section and loose-fitting section comprise different materials.

10. A medical glove as defined in claim 1, wherein a lubricous powder material is disposed on an inner surface of said tight-fitting section.

* * * * *